United States Patent [19]
Furukawa et al.

[11] Patent Number: 6,087,512
[45] Date of Patent: Jul. 11, 2000

[54] PROCESS FOR PREPARATION OF GLYCIDYL ETHER

[75] Inventors: Yoshiro Furukawa, Osaka; Kazuhiro Kitaori, Itami; Tetsuya Yanagimoto; Masafumi Mikami, both of Amagasaki; Hiroshi Yoshimoto, Ibaraki; Junzo Otera, Okayama, all of Japan

[73] Assignee: Daiso Co., Ltd., Osaka, Japan

[21] Appl. No.: 09/147,715

[22] PCT Filed: Sep. 12, 1997

[86] PCT No.: PCT/JP97/03221

§ 371 Date: Apr. 29, 1999

§ 102(e) Date: Apr. 29, 1999

[87] PCT Pub. No.: WO98/12186

PCT Pub. Date: Mar. 26, 1998

[30] Foreign Application Priority Data

Sep. 18, 1996 [JP] Japan ................................ 8-246203

[51] Int. Cl.⁷ ...................... C07D 301/28; C07D 303/23
[52] U.S. Cl. ............................. 549/517; 549/516
[58] Field of Search ..................... 549/516, 517

[56] References Cited

FOREIGN PATENT DOCUMENTS

| | | |
|---|---|---|
| 454385 | 10/1991 | European Pat. Off. . |
| 1-102072 | 4/1989 | Japan . |
| 1-121282 | 5/1989 | Japan . |
| 1-279887 | 11/1989 | Japan . |
| 1-279890 | 11/1989 | Japan . |
| 3-77856 | 4/1991 | Japan . |
| 6-037449B | 5/1994 | Japan . |
| 7-179447 | 7/1995 | Japan . |

OTHER PUBLICATIONS

Shiratsuchi et al., *Chem. Pharm Bull.*, "Synthesis and Activity of Optical Isomers of Nipradilol," 35 (9) 3691–3698 (1987).

Kawamura et al., *Chem. Pharm. Bull.*, "An Efficient Synthesis of the Optical Isomers of Nipradilol," 38 (8) 2092–2096 (1990).

Klunder et al., *J. Org. Chem.*, "Arenesulfonate Derivatives of Homochiral Glycidol: Versatile Chiral Building Blocks for Organic Synthesis," 54, 1295–1304 (1989).

*Primary Examiner*—Ba K. Trinh
*Attorney, Agent, or Firm*—Jacobson, Price, Holman & Stern, PLLC

[57] ABSTRACT

A process for preparation of a glycidyl ether which is characrelized in reacting an epoxy compound of the formula

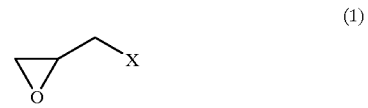

(1)

wherein X is halogen or sulfonyloxy
in the presence of a fluoride salt, with an alcohol. According to the above method, glycigyl ethers or their optically active compounds important as intermediates for synthesis of medicines are easily obtained in good yield and especially the optically active compounds are obtained with highly optical purity.

9 Claims, No Drawings

PROCESS FOR PREPARATION OF GLYCIDYL ETHER

This application is a 371 of PCT/JP97/03221, dated Sep. 12, 1997.

1. TECHNICAL FIELD

The present invention relates to a process for preparation of glycidyl ethers and optical active compounds thereof important as intermediates for synthesis of medicines and physiologically active compounds.

2. BACKGROUND ART

Glycidyl ethers are important intermediates for synthesis of many kinds of medicines. For example, so called β-receptor blocking agents which are often used as circulatory drugs, especially antihypertensive agents and antiarrhythmic agents, are basically prepared from glycidyl ethers.

The glycidyl ethers have been prepared by reacting a corresponding alcohol with an epoxy compound, such as epichlorohydrin or glycidyl p-toluenesulfonate. The reaction of the alcohol with epichlorohydrin or glycidyl p-toluenesulfonate is carried out in the presence of an alkali metal base, such as sodium hydride or sodium hydroxide, or an organic base, such as triethylamine or pyridine, or in the presence of catalyst, such as a mineral acid (e.g., sulfuric acid) or Lewis acid (e.g., tin tetrachloride) to prepare a 3-chloro or tosyloxy-2-propanol derivative and it was treated with a base to prepare a glycidyl ether. However, in case of carrying out in the base i n the former, the epoxy compound, such as epichlorohydrin or glycidyl p-toluenesulfonate must be used in excess and therefore, the reaction is not economical. In case of using a strong base, such as sodium hydride or sodium hydoxide, the after-treatment, such as neutralization is necessary and it is troublesome. In case of using sodium hydride there is a possibility of burning in the after-treatment. On the other hand, in case of the latter in acidic conditions the reaction steps are many and the treatment is troublesome. Furthermore, in case of using an aryl derivative having a substituent unstable in basic conditions, the yield is not good.

By the way, glycidyl ethers have an asymmetric carbon atom and exist in optical isomers. Recently in developing the medicines comprising optical isomers, each isomer is investigated. Therefore, it becomes very important to establish a method to prepare easily an optically active compound with highly optical purity of these compounds. In order to solve such problems, combinations of many kinds of bases with an optically active epichlorohydrin, glycidyl p-toluenesulfonate, or glycidyl m-nitrobenzenesulfonate have been investigated. These methods, for instance, are described in Japanese Patent Publication No. 1-121282, Japanese Patent Publication No. 1-279890, Japanese Patent Publication No. 1-279887, European Patent No. 454385, Japanese Patent Publication B No. 6-37449, Chem. Pharm. Bull., 35, 3691 (1987), Chem. Pharm. Bull., 38, 2092 (1990), J. Org. Chem., 54, 1295 (1989) and so on.

However, in all these methods, marked racemization occurs on the reaction and the optical purity decreases.

Optical purity of an glycidyl ether prepared by reacting p-hydroxyphenylacetoamide and an optically active epichlorohydrin in sodium hydroxide as a base decreases to 90% e.e. and it is not satisfactory.

The present inventors engaged extensively in solving above problems, and found to prepare easily and with good yield a glycidyl ether by reacting an epoxy compound and an alcohol in the presence of a fluoride salt. Furthermore, when an optically active epoxy compound is used, the object compound obtained is also optically active, and marked racemization does not occur on the reaction.

DISCLOSURE OF INVENTION

The present invention relates to a process for preparation of a glycidyl ether of the formula

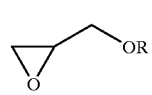

(3)

wherein R is substituted or unsubstituted alkyl, substituted or unsubstituted aryl, or substituted or unsubstituted heterocyclic ring,
which is characterized in reacting an epoxy compound of the formula

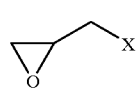

(1)

wherein X is halogen or sulfonyloxy group,
with an alcohol of the formula

ROH (2)

wherein R is as defined above,
in the presence of a fluoride salt.

Examples of halogen shown by X in the formula (1) are chlorine atom, bromine atom and iodine atom, preferably chlorine atom and bromine atom. Examples of sulfonyloxy group shown by X in the formula (1) are preferably a substituted or unsubstituted alkylsulfonyloxy having 1 to 10 carbon atoms, such as methanesulfonyloxy or trifluoromethanesulfonyloxy, a substituted or unsubstituted arylsulfonyloxy, such as benzenesulfonyloxy, p-toluenesulfonyloxy or m-nitrobenzenesulfonyloxy.

Examples of the epoxy compound of the formula (1) are epichlorohydrin, epibromohydrin, glycidyl methanesulfonate, glycidyl trifluoromethanesulfonate, glycidyl ethanesulfonate, glycidyl propanesulfonate, glycidyl butanesulfonate, glycidyl phenylmethanesulfonate, glycidyl p-trifluoromethylbenzenesulfonate, glycidyl benzenesulfonate, glycidyl p-toluenesulfonate, glycidyl 2,4,6-triisopropylbenzenesulfonate, glycidyl p-tert-butylbenzenesulfonate, glycidyl p-chlorobenzenesulfonate, glycidyl p-bromobenzenesulfonate, glycidyl p-iodobenzenesulfonate, glycidyl 2,4,5-trichlorobenzenesulfonate, glycidyl o-nitrobenzenesulfonate, glycidyl m-nitrobenzenesulfonate, glycidyl p-nitrobenzenesulfonate, glycidyl 2,4-dinitrobenzenesulfonate, glycidyl p-methoxybenzenesulfonate, glycidyl 4-chloro-3-nitrobenzenesulfonate, glycidyl 1-naphthalenesulfonate, glycidyl 2-naphthalenesulfonate and so on. Glycidyl m-nitrobenzenesulfonate, glycidyl p-toluenesulfonate and epichlorohydrin are preferably used among them.

Examples of the alcohol of the formula (2) are alkanols having 1 to 10 carbon atoms, such as methanol, ethanol, propanol, butanol, isopropyl alcohol, isobutyl alcohol, t-butyl alcohol, sec-butyl alcohol and the like, alkanols substituted by a phenyl, such as benzyl alcohol, α-phenethyl alcohol, β-phenethyl alcohol and the like, alkanols substituted by a phenyl having substitutent(s), such as p-methoxybenzyl alcohol, p-nitrobenzyl alcohol and the like. Aromatic alcohols are also used, such as phenol and aromatic alcohols having substituent(s). The substituents are not limited as far as they do not prevent this reaction, and include saturated or unsatulated alkyls, such as methy, ethyl, allyl and the like, alkyls having ether bond(s), such as methoxymethyl, 2-methoxyethyl, allyloxymethyl, (2-methoxyethoxy)methyl, (2-isopropoxyethoxy)methyl and the like, nitro, halogen, such as fluorine atom, chlorine atom, bromine atom and iodine atom, trifluoromethyl, alkoxys, such as methoxy, allyloxy, methoxymethoxy and the like, cyano, cyanomethyl, alkoxycarbonyls, such as methoxycarbonyl, ethoxycarbonyl and the like, acyloxys, such as acetoxy and the like, amides, such as acetylamide and the like, carbamoyl, carbamoylmethyl, aldehyde, acyls, such as acetyl, benzoyl and the like. Furthermore, the substituent includes one and more substituents and may form a bridge, such as tetramethylene or methylenedioxy with the other substituent. The substituents, alkyls may be further substituted by another substituent.

The above aromatic alcohol includes a polycyclic aromatic compound having hydroxy. A heterocyclic compound having hydroxy can be also used. Examples of them are polycyclic aromatic alcohols, such as α-naphthol, β-naphthol, 7-hydroxyindene and the like, heterocyclic compounds substituted by hydroxy, such as 3-hydroxypyridine, 3-hydroxytetrahydrofuran, 4-hydroxyindole, 5-hydroxyquinoline and so on.

Preferable alcohols of the formula (2) are aromatic alcohols and heterocyclic compounds having hydroxy, especially o-allylphenol, o-allyloxyphenol, 4-hydroxyindole, p-(2-isopropoxyethoxy)methylphenol, α-naphthol and carbamoylmethylphenol.

The amount of the alcohol of the formula (2) is 0.5 to 3 mole equivalent to epoxy compound (1), preferably 0.8 to 1.2 mole equivalent. To use it more than 3 mole equivalent does not affect, but is not economical. On the other hand, to use it less than 0.5 mole equivalent causes to leave much amount of an unreacted epoxy compound and it is not economical.

Preferable examples of the fluoride salts used in this reaction are quaternary ammonium fluorides, alkali metal fluorides and alkaline earth metal fluorides, especially alkali metal fluorides and alkaline earth metal fluorides. These may be used alone or in combination of them and may be in form being supported on a carrier.

Examples of the quaternary ammonium fluorides are tetramethylammonium fluoride, tetraethylammonium fluoride, tetrabutylammonium fluoride, tetraoctylammonium fluoride, benzyltrimethylammonium fluoride, etc. Examples of the alkali metal fluorides are sodium fluoride, potassium fluoride and cesium fluoride. Examples of the alkaline earth metal fluorides are magnesium fluoride and calcium fluoride. Examples of the carriers are Celite, alumina, silica gel, molecular sieves, its modified material and so on.

The amount of the fluoride salt is 0.5 to 6 mole equivalent to epoxy compound of the formula (1), preferably, 0.9 to 6 mole equivalent. To use it less than 0.5 mole equivalent does not make the reaction complete and to use more than 6 mole equivalent cause difficult to stir the reaction mixture. In case of using a fluoride salt together with an alkali metal hydrogen carbonate or carbonate mentioned below, the amount of the fluoride salt can reduced to 0.05 mole equivalent to the epoxy compound. Even in case of using it less than 0.05 mole equivalent the reaction proceeds, but it takes much hours in the reaction and is not practical.

Examples of solvents used in this reaction are polar aprotic solvents, such as N,N-dimethylformamide, dimethyl sulfoxide, sulforane, hexamethylphosphoramide and the like, esters, such as ethyl acetate, butyl acetate and the like, ethers, such as tetrahydrofuran, 1,4-dioxane, 1,2-dimethoxyethane, t-butylmethyl ether, diethyl ether and the like, ketones, such as acetone, methyl ethyl ketone, methyl isobutyl ketone and the like, nitrites, such as acetonitrile and the like, and a mixture of these solvents. Preferable ones are tetrahydrofuran, t-butylmethyl ether and actonitrile, more preferably N,N-dimethylformamide.

The reaction proceeds without catalyst, but the reaction is accelerated by adding N,N-dimethylaminopyridine, alkali metal or alkaline earth metal halides, such as cesium iodide, potassium bromide, sodium bromide, magnesium bromide, calcium bromide, potassium iodide, sodium iodide, magnesium iodide and calcium iodide, quaternary ammonium salts, such as tetrabutylammonium fluoride, terabutylammonium chloride, benzyltrimethylammonium bromide and the like, crown ethers, such as 18-Crown-6 and the like. The amount of the catalyst is 0.1–50 mole percentage per alcohol (2).

The mechanism of the reaction is not clear, but the reaction proceed in neutral conditions and it seems that the resulting acid is caught by a fluoride salt. In fact, when a week base, such as an alkali metal or alkaline earth metal hydrogen carbonate or carbonate as an acid trapping agent is added, the reaction is accelerated and the amount of the fluoride salt can be reduced. Therefore, it is effective to add an alkali metal or alkaline earth metal hydrogen carbonate or carbonate, such as sodium hydrogen carbonate, potassium hydrogen carbonate, sodium carbonate, potassium carbonate, calcium carbonate, magnesium carbonate, barium carbonate and the like, thereto. Its amount is not limited, but usually 0.1 to 10 mole equivalent to alcohol of the formula (2), preferably 1 to 3 mole equivalent is used.

The reaction temperature is −50° C. to boiling point of the solvent used, preferably −10 to 100° C. In case of the temperature being too low, the reaction rate becomes low, and in case of the temperature being too high, degradation of the starting materials or product occurs and the yield of the product decreases. Furthermore, when an optically active epoxy compound is used, racemization occurs at the reaction temperature of more than 100° C. and therefore, such the high temperature is not preferable.

Regarding post treatment after the reaction, insoluble materials are filtered off, water is added thereto and the object compound is extracted with an organic solvent, or after the removal of insoluble materials, the filtrate may be subjected to, after removal of the solvent, distillation, recrystallization, or column chromatography to prepare the object compound. Therefore, these procedures are very simple and do not need any such complex procedure as the old procedure needs to react carefully the excess strong base with water or diluted hydrochloric acid and make neutralization treatment and extraction.

According to the present invention, in case of using an optically active epoxy compound as a starting material, an optically active glycidyl ether is obtained. In case of using an epoxy compound with highly optical purity, marked racemization does not occur on the reaction there is obtained a glycidyl ether with highly optical purity.

The present invention is explained in detail by following examples.

REFERENCE EXAMPLE 1

Preparation of Potassium Fluoride/Alumina

Potassium fluoride (58.1 g) was dissolved in water (about 300 ml) and powdered alumina (neutral, 100 g) were added thereto. Water was distilled off in vacuo and the residue was dried in vacuo.

REFERENCE EXAMPLE 2

Preparation of Sodium Fluoride/Calcium Fluoride

Sodium fluoride (42.0 g) was dissolved in water (about 300 ml) and calcium fluoride (78.1 g) was added thereto and mixture was stirred well. After removal of water in vacuo the residue was dried in vacuo.

EXAMPLE 1 p-Hydroxyphenyl acetamide (1 g) was dissolved in N,N-dimethylfomamide (DMF, 5 ml) under nitrogen atmosphere and the solution was cooled to 0° C. Cesium fluoride (3.02 g) was added thereto, and the mixture was stirred for 1 hour. Then, S-glycidyl m-nitrobenzenesulfonate (1.71 g, 99.3% e.e.) was added thereto and the mixture was stirred for 12 hours at the same temperature. After the reaction, water was added to the mixture, the mixture was extracted with ethyl acetate, dried over anhydrous magnesium sulfate, condensed and the residue was subjected to silica gel chromatography (hexane/ethyl acetate; 1:1) to give 1.31 g of (S)-1-[p-(carbamoylmethyl)phenoxy]-2,3-epoxypropane (yield 96%, optical purity 99.3% e.e.) as colorless crystals.

m.p. 167.8–169.1° C.

$[\alpha]_D$(21° C., c=0.5, $CH_3OH$)=+10.9°

NMR(DMSO-d6) δ:2.65–2.73(1H, m), 2.83(1H, dt), 3.29 (1H, s), 3.33(1H, m), 3.80(1H, ddd), 4.29(1H, ddd), 6.82 (1H, brs), 6.89(2H, d), 7.17(2H, d), 7.39(1H, brs)

EXAMPLE 2

Phenol (1.09 g) was dissolved in DMF (5 ml) under nitrogen atmosphere and the solution was cooled to 0° C. Cesium fluoride (2.29 g) was added thereto, and the mixture was stirred for 1 hour. Then, R-glycidyl m-nitrobenzenesulfonate (3.0 g, 99.3% e.e.) was added thereto and the mixture was stirred for 12 hours at the same temperature. After the reaction, water was added to the mixture, the mixture was extracted with ethyl acetate, dried over anhydrous magnesium sulfate, condensed and the residue was subjected to silica gel chromatography (hexane/ethyl acetate; 50:1) to give 1.55 g of (R)-2,3-epoxyphenol (yield 89%, optical purity 98.5% e.e.) as a colorless oil.

$[\alpha]_D$(21° C., c=2.86, $CH_3OH$)=−15.1°

NMR(CDCl3) δ:2.76(1H, m), 2.90(1H, m), 3.30–3.45 (1H, m), 3.96(1H, dd), 4.21(1H, m), 6.85–7.09(3H, m), 7.21–7.41(2H, m)

EXAMPLE 3 o-Allyloxyphenol (1.0 g) was dissolved in DMF (5 ml) under nitrogen atmosphere and the solution was cooled to 0° C. Cesium fluoride (1.52 g) was added thereto and the mixture was stirred for 1 hour. Then, R-glycidyl m-nitrobenzenesulfonate (1.73 g, 99.3% e.e.) was added thereto and the mixture was stirred for 12 hours at the same temperature. After the reaction, water was added to the mixture, the mixture was extracted with ethyl acetate, dried over anhydrous magnesium sulfate, condensed and the residue was subjected to silica gel chromatography (hexane/ethyl acetate; 3:2) to give 1.32g of (R)-3-[o-allyoxyphenoxy]-1,2-epoxypropane (yield 96%, optical purity 99.3% e.e.) as a colorless oil.

$[\alpha]_D$(21° C., c=1.0, $CH_3OH$)=−15.0°

NMR(CDCl3) δ:2.75, 2.87(2H, 2q), 3.34(1H, m), 4.03, 4.25(2H, 2q), 4.59(2H, m), 5.27, 5.41(2H, 2q), 6.08(1H, 2q), 6.87–6.98(4H, m)

EXAMPLE 4

1-Naphthol (1.0 g) was dissolved in DMF (8 ml) under nitrogen atmosphere and the solution was cooled to 0° C. Cesium fluoride (2.11 g) was added thereto and the mixture was stirred for 1 hour. Then, (S)-glycidyl m-nitrobenzenesulfonate (1.80 g, 99.3% e.e.) was added thereto and the mixture was stirred for 24 hours at the same temperature. After the reaction, water was added to the mixture, the mixture was extracted with ethyl acetate, dried over anhydrous magnesium sulfate, condensed and the residue was subjected to silica gel chromatography (hexane/ethyl acetate; 6:1) to give 1.34 g of (S)-1-(2,3-epoxypropoxy)naphthalene (yield 96.5%, optical purity 99.2% e.e.) as a colorless oil.

$[\alpha]_D$ (21° C., c=1.0, $CHCl_3$)=+16.9°

NMR(CDCl3) δ:2.85(1H, m), 2.96(1H, m), 3.43–3.51 (1H, m), 4.11(1H, dd), 4.40(1H, m), 6.80(1H, d), 7.32–7.52 (4H, m), 7.74–7.83(1H, m), 8.24–8.34(2H, m)

EXAMPLE 5

4-Hydroxyindole (3.0 g) was dissolved in DMF (10 ml) under nitrogen atmosphere and the solution was cooled to 0° C. Cesium fluoride (10.12 g) was added thereto and the mixture was stirred for 1 hour. Then (S)-glycidyl m-nitrobenzenesulfonate (5.84 g, 99.3% e.e.) was added thereto and the mixture was stirred for 30 hours at the same temperature. After the reaction, water was added to the mixture, the mixture was extracted with ethyl acetate, dried over anhydrous magnesium sulfate, condensed and the residue was subjected to silica gel chromatography (hexane/isopropyl alcohol; 20:1) to give 4.01 g of (S)-4-(2,3-epoxypropoxy)indole (yield 94.1%, optical purity 99.2% e.e.) as a colorless oil.

$[\alpha]_D$ (24° C., c=0.5, $CH_3OH$)=+28.2°

NMR(CDCl3) δ:2.66(1H, dd), 2.77(1H, t), 3.27–3.33(1H, m), 3.94(1H, dd), 4.22(1H, dd), 6.38(1H, d), 6.55–6.57(1H, m), 6.84–7.00(3H, m), 8.20(1H, brs)

EXAMPLE 6

4-Hydroxyphenylacetamide (1 g) was dissolved in DMF (10 ml) under nitrogen atmosphere and the solution was cooled to 0° C. Cesium fluoride (2.01 g) was added thereto and the mixture was stirred for 1 hour. Then, (S)-glycidyl p-toluenesulfonate (1.50 g, 98.9% e.e.) was added thereto and the mixture was stirred for 30 hours at the same temperature. After the reaction, water was added to the mixture, the mixture was extracted with ethyl acetate, dried over anhydrous magnesium sulfate, condensed and the residue was subjected to silica gel chromatography (hexane/ethyl acetate; 1:1) to give 1.16 g of (S)-1-[p-carbamoylmethyl)phenoxy]-2,3-epoxypropane (yield 84.7%, optical purity 98.0% e.e.) as colorless crystals.

EXAMPLE 7 p-Hydroxyphenylacetamide (1 g) was dissolved in DMF (5 ml) under nitrogen atmosphere and the solution was cooled to 0° C. Cesium fluoride (3.02 g) and sodium iodide (0.1 g) were added thereto and the mixture was stirred for 1 hour. Then (R)-epichlorohydrin (0.62 g, 98.4% e.e.) was added thereto and the mixture was stirred for 30 hours at the same temperature. After the reaction, water was added to the mixture, the mixture was extracted with ethyl acetate, dried over anhydrous magnesium sulfate, condensed and the residue was subjected to silica gel chromatography (hexane/ ethyl acetate; 1:1) to give 1.22 g of (S)-1-[p-carbamoylmethyl)phenoxy]-2,3-epoxypropane (yield 89%, optical purity 98.0% e.e.) as colorless crystals.

EXAMPLE 8

4-Hydroxyphenylacetamide (1 g) was dissolved in DMF (10 ml) under nitrogen atmosphere and the solution was cooled to 0° C. Cesium fluoride (0.20 g) and potassium carbonate (1.19 g) were added thereto and the mixture was stirred for 1 hour. Then (S)-glycidyl m-nitrobenzenesulfonate (1.71 g, 99.3% e.e.) was added thereto and the mixture was stirred for 12 hours at the same temperature. After the reaction inorganic materials were filtered off, and water was added to the filtrate. The mixture was extracted with ethyl acetate, dried over anhydrous magnesium sulfate, condensed and the residue was subjected to silica gel chromatography (hexane/ethyl acetate; 1:1) to give 1.29 g of (S)-1-[p-carbamoylmethyl)phenoxy]-2,3-epoxypropane (yield 94.2%, optical purity 99.2% e.e.) as colorless crystals.

EXAMPLE 9 o-Allyloxyphenol (1.0 g) was dissolved in tetrahydrofuran (THF, 10 ml) under nitrogen atmosphere and the solution was cooled to 0° C. Potassium fluoride (1.55 g) and 18-Crown-6 (0.17 g) were added thereto and the mixture was stirred for 1 hour. Then (R)-glycidyl m-nitrobenzenesulfonate (1.73 g, 99.3% e.e.) was added thereto and the mixture was stirred for 40 hours at the same temperature. After the reaction, water was added to the mixture, the mixture was extracted with ethyl acetate, dried over anhydrous magnesium sulfate, condensed and the residue was subjected to silica gel chromatography (hexane/ ethyl acetate; 3:2) to give 1.07 g of (R)-3-(o-allyloxyphenoxy)-1,2-epoxypropane (yield 78%, optical purity 96.26% e.e.) as a colorless oil.

EXAMPLE 10 o-Allyloxyphenol (1.0 g) was dissolved in THF (10 ml) under nitrogen atmosphere and the solution was cooled to 0° C. Potassium fluoride (1.55 g) and tetrabutyl ammonium fluoride (0.2 g) were added thereto and the mixture was stirred for 1 hour. Then, (R)-glycidyl m-nitrobenzenesulfonate (1.73 g, 99.3% e.e.) was added thereto and the mixture was stirred for 40 hours at the same temperature. After the reaction, water was added to the mixture, the mixture was extracted with ethyl acetate, dried over anhydrous magnesium sulfate, condensed and the residue was subjected to silica gel chromatography (hexane/ ethyl acetate; 3:2) to give 0.96 g of (R)-3-(o-allyloxyphenoxy)-1,2-epoxypropane (yield 70%, optical purity 95.9% e.e.) as a colorless oil.

EXAMPLE 11 o-Allyloxyphenol (1.0 g) was dissolved in acetonitrile (15 ml) under nitrogen atmosphere and the solution was cooled to 0° C. Potassium fluoride/alumina (2 g) prepared in Reference Example 1 was added thereto and the mixture was stirred for 1 hour. Then, (R)-glycidyl m-nitrobenzenesulfonate (1.73 g, 99.3% e.e.) was added thereto and the mixture was stirred for 30 hours at the same temperature. After the reaction, a solid material was filtered off and water was added to the filtrate. The solution was extracted with ethyl acetate, dried over anhydrous magnesium sulfate, condensed and the residue was subjected to silica gel chromatography (hexane/ethyl acetate; 3:2) to give 1.22 g of (R)-3-(o-allyoxyphenoxy)-1,2-epoxypropane (yield 89%, optical purity 98.0% e.e.) as a colorless oil.

EXAMPLE 12 o-Allyloxyphenol (1.0 g) was dissolved in DMF (15 ml) under nitrogen atmosphere and the solution was cooled to 0° C. Potassium fluoride/calcium fluoride (4 g) prepared in Reference Example 2 were added thereto, and the mixture was stirred for 1 hour. Then, (R)-glycidyl m-nitrobenzenesulfonate (1.73 g, 99.3% e.e.) was added thereto and the mixture was stirred for 38 hours at the same temperature. After the reaction, a solid material was filtered off and water was added to the filtrate. The solution was extracted with ethyl acetate, dried over anhydrous magnesium sulfate, condensed and the residue was subjected to silica gel chromatography (hexane/ethyl acetate; 3:2) to give 0.82 g of (R)-3-(o-allyoxyphenoxy)-1,2-epoxypropane (yield 60%, optical purity 98.0% e.e.) as a colorless oil.

EXAMPLE 13 p-(2-Isopropoxyethoxy)methylphenol (5 g) was dissolved in DMF (30 ml) under nitrogen atmosphere and the solution was cooled to 0° C. Cesium fluoride (0.72 g) and potassium carbonate (4.27 g) were added thereto, and the mixture was stirred for 1 hour. Then (S)-glycidyl m-nitrobenzenesulfonate (6.16 g, 99.7% e.e.) was added thereto and the mixture was stirred for 24 hours at the same temperature. After the reaction, water was added to the filtrate, the solution was extracted with ethyl acetate, dried over anhydrous magnesium sulfate, condensed and the residue was subjected to silica gel chromatography (hexane/ ethyl acetate; 1:1) to give 6.08 g of (S)-1-(p-2-isopropoxyethoxymethylphenoxy)-2,3-epoxypropane (yield 96%, optical purity 99.6% e.e.) as a colorless oil.

$[\alpha]_D$ (21° C., c=1.0, $CH_3OH$)=+9.5°

NMR(CDCl3) δ:1.17(6H, d), 2.75(1H, dd), 2.90(1H, t), 3.32–3.37(1H, m), 3.58–3.68(5H, m), 3.95(1H, dd), 4.21 (1H, dd), 4.51(2H, s), 6.88–7.29(4H, m)

EXAMPLE 14

4-(2-Isopropoxyethoxy)methylphenol (2.10 g) was dissolved in DMF (7.5 ml) under nitrogen atmosphere. Tetrabutylammonium fluoride (7.84 g) was added thereto and the mixture was stirred for 1 hour. Then, (S)-glycidyl m-nitrobenzenesulfonate (2.59 g, 99.3% e.e.) was added thereto and the mixture was stirred for 40 hours at room temperature. After the reaction, water was added to the mixture, the mixture was extracted with ethyl acetate, dried over anhydrous magnesium sulfate, condensed and the residue was subjected to silica gel chromatography (hexane/ ethyl acetate; 3:2) to give 1.76 g of (S)-3-[4-(2 -isopropoxyethoxy)methyl]phenoxy-1,2-epoxypropane (yield 66%, optical purity 97.3% e.e.) as a colorless oil.

EXAMPLE 15

4-(2-Isopropoxyethoxy)methylphenol (2.10 g) was dissolved in DMF (7.5 ml) under nitrogen atmosphere. Potassium carbonate (1.80 g) and tetrabutylammonium fluoride (523 mg) were added thereto and the mixture was stirred for 1 hour. Then (S)-glycidyl m-nitrobenzenesulfonate (2.59 g, 99.3% e.e.) was added thereto and the mixture was stirred for 48 hours at room temperature. After the reaction, water was added to the mixture, the mixture was extracted with ethyl acetate, dried over anhydrous magnesium sulfate, condensed and the residue was subjected to silica gel chromatography (hexane/ethyl acetate; 3:2) to give 2.48 g of (S)-3-[4-(2-isopropoxyethoxy)methyl]phenoxy-1,2-epoxypropane (yield 93%, optical purity 97.7% e.e.) as a colorless oil.

COMPARATIVE EXAMPLE 1 p-Hydroxyphenyl acetamide (30.02 g) was dissolved in 106.5 g of water containing sodium hydroxide (9.6 g) and the solution was cooled to 5° C. Epichlorohydrin (18.5 g, 98.9% e.e.) was dropped in the solution over a period of 10 minutes under stirring at the same temperature and the solution was stirred for 24 hours. Sodium hydroxide (2.4 g) was added thereto and the mixture was stirred for 5 hours. Resulting crystals were filtrated by suction, washed with water and dried in vacuo to give crude (S)-1-[p-(carbamoylmethyl)phenoxy]-2,3-epoxypropane (39.8 g). The optical purity of it was 91.2% e.e. by measurement of Chiral column OD (Daisel Chemical Industries Ltd.).

COMPARATIVE EXAMPLE 2 o-Allyloxyphenol (1 g) was dissolved in DMF (5 ml) under nitrogen atmosphere and the solution was cooled to 0° C. Sodium hydride (0.32 g, 60% in oil), after the oil therein was washed with hexane, was added the solution under stirring for 30 minutes. Then, 1.52 g of (R)-glycidyl p-toluenesulfonate (98.5% e.e.) dissolved in DMF (5 ml) was dropped in over a period of 30 minutes and stirred for 9 hours. After the reaction, thereto ice water was added, neutralized with 0.1% hydrochloric acid, and extracted with ethyl acetate. The extract was washed with saturated brine, dried over anhydrous magnesium sulfate and condensed to give 1.35 g of crude (R)-3-(o-allyloxyphenoxy-1,2-epoxypropane. The optical purity of it was 92.6% e.e. by measurement of Chiral column OD (Daisel Chemical Industries Ltd.).

COMPARATIVE EXAMPLE 3 p-Hydroxyphenylacetamide (1 g) and (S)-glycidyl p-toluenesulfonate (1.51 g, 99.3% e.e.) were dissolved in acetone (30 ml). Potassium carbonate (1.19 g) was added to the solution and the solution was stirred for 30 hours under refluxing. After the reaction, inorganic materials were filtered off and acetone was removed to give 1.43 g of crude (S)-1-[p-(carbamoylmethyl)phenoxy-2,3-epoxypropane. The optical purity of it was 62.8% e.e. by measurement of Chiral column OD (Daisel Chemical industries Ltd.).

According to the present invention, glycidyl ethers important as intermediates for synthesis of medicines and physiologically active compounds are prepared very easily and with good yield. Especially in case of using an optically active epoxy compound, there is obtained the object compound with highly optical purity without any marked racemization.

We claim:
1. A process for preparation of a glycidyl ether of the formula

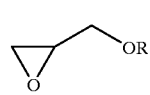
(3)

wherein R is substituted or unsubstituted alkyl, substituted or unsubstituted aryl, or substituted or unsubstituted heterocyclic ring,
which is characterized in reacting an epoxy compound of the formula

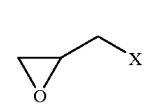
(1)

wherein X is halogen or sulfonyloxy group,
with an alcohol of the formula

ROH  (2)

wherein R is as defined above,
in the presence of a fluoride salt.

2. The process for preparation of a glycidyl ether of claim 1 which is characterized in reacting in the presence of a fluoride salt, and an alkali metal or alkaline earth metal hydrogen carbonate or carbonate.

3. The process for preparation of a glycidyl ether claim 1 which is characterized in reacting in the presence of a compound selected from an alkali metal or alkaline earth metal halides, quaternary ammonium halides and crown ethers.

4. The process for preparation of a glycidyl ether of claim 1 wherein the epoxy compound (1) is glycidyl m-nitrobenzenesulfonate, glycidyl p-toluenesulfonate or epichlorohydrin.

5. The process for preparation of a glycidyl ether of claim 1 wherein the alcohol (2) is one having a substituted or unsbstituted aromatic ring, or a substituted or unsubstituted heterocyclic ring.

6. The process for preparation of a glycidyl ether of claim 1 wherein the alcohol (2) is phenol or a phenol derivative.

7. The process for preparation of glycidyl ether of claim 1 wherein the alcohol (2) is o-allylphenol, o-allyloxyphenol, 4-hydroxyindole, p-(2-isoprpoxyethoxy)mehylphenol, α-naphthol or p-carbamoylmethylphenol.

8. The process for preparation glycidyl ether of claim 1 wherein the fluoride salt is an alkali metal or alkaline earth metal fluoride.

9. The process for preparation of a glycidyl ether of claim 1 which is characterized in preparing an optically active glycidyl ether from an optically active epoxy compound.

* * * * *